US006407260B1

United States Patent
Bonaventure et al.

(10) Patent No.: US 6,407,260 B1
(45) Date of Patent: Jun. 18, 2002

(54) INDOLE COMPOUND

(75) Inventors: Nicole Bonaventure, Vincennes; Patrick Gilard; Gilles Barre, both of Villepinte; Michel Dubois, Pommeuse, all of (FR)

(73) Assignee: L'Oréal S.A., Paris (FR)

( * ) Notice: Subject to any disclaimer, the term of this patent is extended or adjusted under 35 U.S.C. 154(b) by 38 days.

(21) Appl. No.: 09/666,465

(22) Filed: Sep. 20, 2000

(30) Foreign Application Priority Data

Sep. 22, 1999 (FR) ............................................. 99 11833

(51) Int. Cl.$^7$ ...................... C07D 487/14; C07D 487/22
(52) U.S. Cl. ...................... 548/416; 548/417; 548/418; 8/404; 8/505; 8/423
(58) Field of Search ...................... 8/407, 409, 423, 8/421, 405; 548/484, 371.4, 416, 417, 418

(56) References Cited

U.S. PATENT DOCUMENTS

| | | | |
|---|---|---|---|
| 4,961,754 A | | 10/1990 | Grollier ............................ 8/423 |
| 4,964,754 A | * | 10/1990 | Grollier ............................ 8/423 |
| 5,112,360 A | * | 5/1992 | Garoche et al. ................ 8/406 |
| 5,468,872 A | * | 11/1995 | Glicksman et al. .......... 548/416 |
| 5,616,724 A | * | 4/1997 | Hudkins et al. .............. 548/417 |
| 5,690,697 A | * | 11/1997 | Samain ............................ 8/423 |
| 5,695,747 A | * | 12/1997 | Forestier et al. ............... 424/59 |
| 5,704,948 A | * | 1/1998 | Terranova et al. .............. 8/409 |
| 5,752,982 A | * | 5/1998 | Lang et al. ...................... 8/409 |
| 5,755,829 A | * | 5/1998 | Terranova et al. .............. 8/409 |
| 5,938,792 A | * | 8/1999 | Lang et al. ...................... 8/409 |
| 6,002,018 A | * | 12/1999 | Terranova et al. ............ 548/484 |
| 6,203,580 B1 | * | 3/2001 | Vandenbossche et al. ...... 8/421 |
| 6,099,593 A1 | * | 8/2001 | Terranova et al. .............. 8/409 |
| 6,118,008 A1 | * | 9/2001 | Malle et al. ............... 548/371.4 |
| 6,309,426 B1 | * | 10/2001 | Dias et al. ........................ 8/407 |

FOREIGN PATENT DOCUMENTS

| | | | |
|---|---|---|---|
| EP | 1086951 A1 | * | 3/2001 |
| FR | 2 618 069 | | 1/1989 |
| FR | 2 677 544 | | 12/1992 |

OTHER PUBLICATIONS

Paola Manini et al., "Acid–Promoted Competing Pathways in the Oxidative Polymerization of 5,6–Dihydroxindoles and Related Compounds: Straightforward Cyclotrimerization Routes to Diindolocarbazole Derivatives", J. Org. Chem, vol. 63, No. 20, 1998, pp. 7002–7008.

\* cited by examiner

*Primary Examiner*—Lorna M. Douyon
*Assistant Examiner*—Ann-Marie Koss
(74) *Attorney, Agent, or Firm*—Finnegan, Henderson, Farabow, Garrett & Dunner, L.L.P.

(57) ABSTRACT

The invention relates to novel indole compounds, to their use as direct dyes in compositions intended for dyeing keratin materials and for example compositions intended for dyeing human keratin fibers and including the hair, and in cosmetic compositions intended for making up the skin, the nails and the lips, to the dye compositions or make-up compositions comprising them and to the direct dyeing process using them, and processes of manufacturing said novel indole compounds.

14 Claims, No Drawings

INDOLE COMPOUND

The invention relates to novel indole compounds, to their use as direct dyes in compositions intended for dyeing keratin materials and for example compositions intended for dyeing human keratin fibres and including the hair, and in cosmetic compositions intended for making up the skin, the nails and the lips, to the dye compositions and make-up compositions comprising them and to the corresponding direct dyeing process.

In the field of hair dyeing, direct dyes are sought, i.e. dyes which, without supplying an oxidizing agent, are capable by themselves of temporarily modifying the natural shade of the hair. In this application, the dyes may satisfy a certain number of criteria, and for example they may generate rich and varied shades making it possible to obtain a wide range of colours likely to satisfy the formulator; in this perspective, novel compounds are always being sought to be able to dye in a range of colours extending for example from orange to red. Moreover, the dyeing results obtained may be reproducible, strong and resistant to washing, rubbing, permanent-waving, light and perspiration.

The inventors have now discovered, entirely surprisingly and unexpectedly, novel indole compounds of formula (I) defined below, in the range of shades from orange to red, which are suitable for use as direct dyes in the dyeing of keratin materials, and in make-up compositions for the skin, the nails and the lips.

These novel dyes can also make it possible to obtain strong orange to red shades which show excellent properties of resistance to one or more of the various treatments to which keratin fibres may be subjected, and for example the hair, with respect to light, washing, permanent-waving and perspiration.

These discoveries form the basis of the present invention.

A first subject of the invention is thus a novel compound of formula (I):

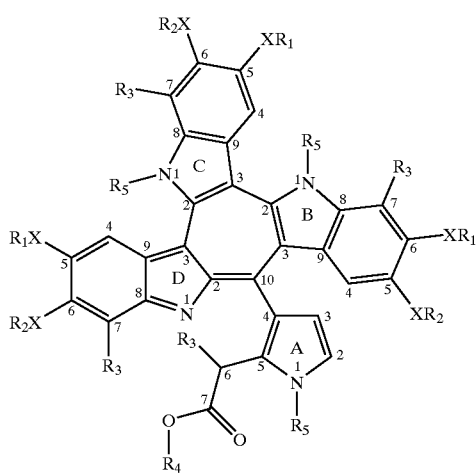

wherein:
- X, which may be identical or different, are each chosen from oxygen atoms and nitrogen atoms;
- $R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl($C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;
- $R_3$, $R_4$ and $R_5$, which may be identical or different, are each chosen from hydrogen atoms and linear and branched, saturated and unsaturated $C_1$–$C_4$ hydrocarbons.

In formula (I) according to the invention, said alkyl groups are chosen from linear groups and branched groups and include, for example, methyl groups, ethyl groups, n-propyl groups, isopropyl groups, n-butyl groups, isobutyl groups and tert-butyl groups; said $C_1$–$C_4$ monohydroxyalkyl groups include, for example, —$CH_2$—$CH_2OH$ groups and said $C_1$–$C_4$ polyhydroxyalkyl groups include, for example, —CHOH—$CH_2OH$ groups.

Among the indole compounds of formula (I), the compound of formula (II) is an example:

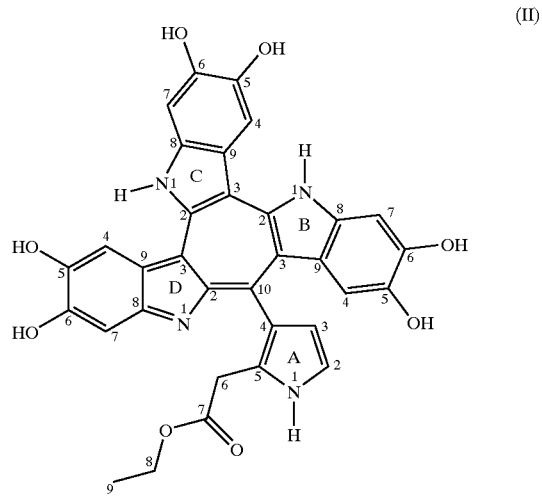

A subject of the invention is also a process for manufacturing an indole compound of formula (I) according to the invention comprising oxidation of the corresponding indole in a solvent medium according to oxidation processes that are generally well known to those skilled in the art.

In this way, a compound of formula (III):

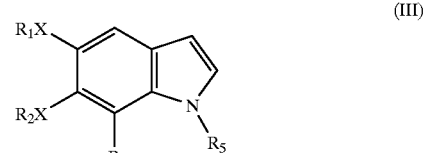

wherein $R_1$, $R_2$, $R_3$, $R_5$ and X have the same meanings as defined in formula (I) above, may be oxidized in alcoholic medium (methanol, ethanol, n-propanol, isopropanol, n-butanol and tert-butanol, for example). Additionally, said oxidation may be at room temperature. Further additionally, said oxidation may occur in the presence of sodium metaperiodate, to give a compound of formula (I) according to the invention.

Said sodium metaperiodate may also be replaced with appropriate sodium metaperiodate substitutes. Said substitutes may be chosen from, for example, molecular oxygen, hydrogen peroxide, potassium permanganate, selenium oxide and peracids. Said sodium metaperiodate and said appropriate substitutes may also be in the presence of metal catalysts which may be chosen from, for example, manganese, iron and chromium.

A subject of the invention is also a process for manufacturing an indole compound of formula (I) according to the invention, comprising oxidation of a compound of formula (III) described above in an alcoholic medium, in the presence of sodium metaperiodate, and at room temperature.

A subject of the invention is also a process of manufacturing a direct dye comprising including in said dyes at least one composition comprising at least one of said indole compounds of formula (I) according to the invention.

A subject of the invention is also a process of manufacturing make-up products comprising including in said make-up products at least one composition comprising at least one of said indole compounds of formula (I) according to the invention.

A subject of the invention is also a direct dye composition for keratin materials, comprising a medium suitable for dyeing and an effective amount of at least one compound of formula (I) according to the invention.

A subject of the invention is also a make-up product composition for keratin materials, comprising a medium suitable for make-up products and an effective amount of at least one compound of formula (I) according to the invention.

For the purposes of the present invention, the expression "keratin materials" mainly means the skin of the face and the body, the lips, the nails, at least one human keratin fiber such as human hair, body hairs, eyelashes and eyebrows, and also at least one keratin fiber such as natural textile fibers, including wool.

A subject of the invention is, for example, a direct dye composition for human keratin fibers such as the hair, comprising a medium suitable for dyeing and an effective amount of at least one compound of formula (I) according to the invention.

However, other non-limiting characteristics, aspects and advantages of the invention will emerge even more clearly on reading the description which follows, as well as the various concrete, but in no way limiting, examples intended to illustrate it.

When said composition is intended for dyeing, the compound(s) of formula (I) according to the invention can be each chosen from a range from approximately 0.05% to approximately 10% by weight relative to the total weight of the dye composition, and also from a range from approximately 0.05% to approximately 0.5% by weight relative to this weight.

When said composition is intended for make-up, the compound(s) of formula (I) according to the invention can be each chosen from a range from approximately 0.05% to approximately 20% by weight relative to the total weight of said composition, and also from a range from approximately 0.05% to approximately 5% by weight relative to this weight.

The compounds of formula (I) according to the invention can also serve, in well-known processes of oxidation dyeing of human keratin fibers, using oxidation dyes (oxidation dye precursors and optionally couplers), to shade the dyeing results obtained with the oxidation dyes or to enrich them with glints.

The dye composition according to the invention can also comprise, to broaden the range of shades and to obtain varied colours, besides the orange to red compounds of formula (I) according to the invention, other direct dyes conventionally used, for example nitrobenzene dyes, such as nitrophenylenediamines, nitrodiphenylamines, nitroanilines, nitrophenol ethers and nitrophenols, nitropyridines, anthraquinone dyes, monoazo dyes, diazo dyes, triarylmethane, azine, acridine and xanthene dyes, and alternatively metalliferous dyes.

The proportion of other additional said direct dyes can range from approximately 0.5% to approximately 10% by weight relative to the total weight of the dye composition.

The medium which is suitable for dyeing (or support) may generally comprise water or of a mixture of water and at least one organic solvent to dissolve compounds which may not be sufficiently soluble in water. Organic solvents which can be added to said composition, for example, are $C_1$–$C_4$ lower alkanols such as ethanol and isopropanol; glycerol; glycols and glycol ethers such as 2-butoxyethanol, propylene glycol, propylene glycol monomethyl ether and aromatic alcohols such as benzyl alcohol and phenoxyethanol, similar products and mixtures thereof.

The medium which is suitable for dyeing (or support) may also comprise fatty substances such as oils and waxes.

The solvents may be present in proportions ranging from approximately 1% to approximately 70% by weight relative to the total weight of the dye composition, and also ranging from approximately 5% to approximately 40% by weight.

Fatty amides such as mono- and diethanolamides of acids derived from copra, of lauric acid and of oleic acid can also be added to said composition according to the invention, at concentrations ranging from approximately 0.05% to approximately 10% by weight.

Surfactants, including those that are well known in the state of the art, can also be added to said composition according to the invention. Surfactants may be chosen from, for example, anionic types, cationic types, nonionic types, amphoteric types and zwitterionic types and mixtures thereof. Surfactants can be added to said composition in a proportion ranging from approximately 0.1% to approximately 50% by weight and also can range from approximately 1% to approximately 20% by weight relative to the total weight of said composition.

Thickeners can also be added to said composition according to the invention, in a proportion ranging from approximately 0.2% to approximately 5% by weight relative to the total weight of said composition.

Said dye composition can also comprise common adjuvants, wherein said adjuvants may be chosen from, for example, antioxidants, fragrances, sequestering agents, dispersants, hair conditioners, preserving agents and opacifiers, as well as any other adjuvants commonly used in the dyeing of keratin materials.

A person skilled in the art may select optional additional compound(s) mentioned above, such that the advantageous properties intrinsically associated with the dye composition may not, or may not substantially, be adversely affected by the addition(s) envisaged.

Said dye composition intended for dyeing keratin fibers may have a pH ranging generally from approximately 3 to approximately 12, and can range from approximately 5 to approximately 11. Said pH can be adjusted to the desired value by means of acidifying agents and basifying agents commonly used in the dyeing of keratin fibers.

Said acidifying agents which may be chosen include, for example, inorganic and organic acids such as hydrochloric acid, orthophosphoric acid, sulphuric acid, carboxylic acids such as acetic acid, tartaric acid, citric acid and lactic acid, and sulphonic acids.

Said basifying agents which may be chosen include, for example, aqueous ammonia, alkaline carbonates, alkanolamines such as mono-, di- and triethanolamine and derivatives thereof, sodium hydroxide, potassium hydroxide and the compounds of formula (IV) below:

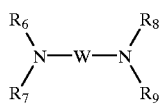

wherein

W is a propylene residue optionally substituted with groups chosen from hydroxyl groups and $C_1$–$C_6$ alkyl groups;

$R_6$, $R_7$, $R_8$ and $R_9$, which may be identical or different, are each chosen from hydrogen atoms, $C_1$–$C_6$ alkyl groups and $C_1$–$C_6$ hydroxyalkyl groups.

Dye compositions according to the invention can be in various forms, such as in the form of liquids, creams, gels and poultices, and in any other form which is suitable for dyeing keratin materials, and including human hair. For example, it can be packaged under pressure in an aerosol can in the presence of a propellant and can form a mousse.

Cosmetic compositions according to the invention intended for make-up may be chosen from, for example, make-up products for the face and the lips such as eyeshadows, face powders, powders and blushers, foundations, lipsticks and lip glosses and make-up products for the human body; they may also be make-up products for the eyelashes, the eyebrows and the nails, such as mascaras, eyebrow pencils, eyeliners and nail varnishes.

Another subject of the invention relates to a cosmetic process for treating at least one keratin fiber, for example human keratin fibers such as the hair and the nails, by direct dyeing, comprising applying to said at least one keratin fiber a composition comprising at least one compound of formula (I) according to the invention. In addition, said cosmetic process may include contact with wet or dry keratin fibers.

Said composition according to the invention can be used as a leave-in composition, i.e. after application of said composition to said fibers, said fibers may be dried without intermediate rinsing.

In other application methods, after applying said composition to said fibers for an exposure time ranging from approximately 3 to approximately 60 minutes, or ranging from approximately 5 to approximately 45 minutes, said fibers are rinsed, optionally washed and then rinsed again and dried.

Another subject of the invention relates to a composition for skin, for mucous membranes, or for keratin fibers comprising at least one compound of formula (I) according to the invention.

Another subject of the invention relates to a direct-dye composition comprising at least one compound of formula (I) according to the invention.

Another subject of the invention relates to a body hygiene composition; a hair composition; a make-up composition; a care composition; an anti-sun composition; or a self-tanning composition comprising at least one compound of formula (I) according to the invention.

Another subject of the invention relates to a composition for support comprising a medium suitable for support and at least one compound of formula (I) according to the invention.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

Concrete and non-limiting examples illustrating the invention will now be given.

PREPARATION EXAMPLE 1

To prepare the compound of formula (II) below:

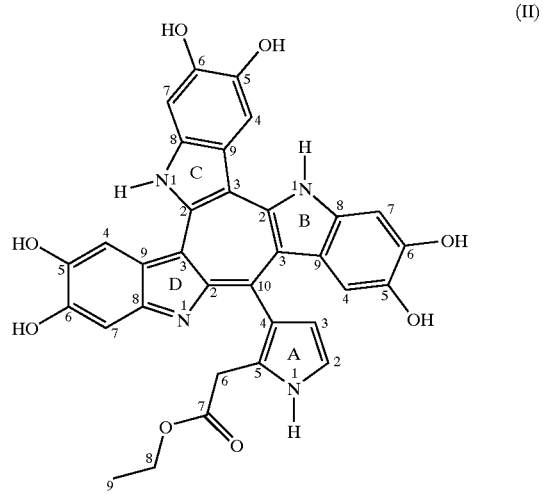

5 grams (0.033 mol) of 5,6-dihydroxyindole were dissolved in 100 grams of ethanol. 7.18 grams (0.033 mol) of sodium metaperiodate were added. The mixture was left stirring at room temperature for 8 hours. After centrifugation and washing, the organic phases were combined and evaporated to dryness.

The compound of formula (II) was isolated by preparative HPLC chromatography. After drying at 40° C., 50 mg of red crystals were isolated.

The structure of the compound was determined by $^1H$, $^{13}C$ and $^{15}N$ 1D NMR and by $^1H$—$^{13}C$ and $^1H$—$^{15}N$ 2D NMR and by mass spectrometry.-

NMR: $^{13}$C NMR Spectrum (solvent: CD$_3$OD-d$_4$, reference: central signal of the solvent at 49.00 ppm): the $^{13}$C chemical shifts, the multiplicities (s: singlet, d: doublet, t: triplet, q: quartet) and the assignments are given in the table below:

| | $^{13}$C chemical shifts | |
|---|---|---|
| δ in ppm | Multiplicity | Assignment |
| 13.83 | q | C-9 A |
| 32.97 | t | C-6 A |
| 62.02 | t | C-8 A |
| 97.89 | d | C-7 D |
| 99.02 | d | C-7 B |
| 99.47 | d | C-7 C |
| 107.65 | d | C-4 D |
| 108.57 | d | C-4 C |
| 109.51 | d | C-3 A |
| 111.23 | d | C-4 B |
| 115.09 | s | C-3 C |
| 116.18 | s | C-3 D |
| 116.37 | s | C-9 D |
| 117.09 | s | C-9 C |
| 118.10 | s | C-9 B |
| 119.36 | s | C-4 A |
| 121.12 | d | C-2 A |
| 122.59 | s | C-5 A |
| 128.73 | s | C-3 B |
| 133.33 | s | C-10 A |
| 137.56 | s | C-5 B |
| 137.67 | s | C-5 C |
| 137.73 | s | C-5 D |
| 139.76 | s | C-2 D |
| 140.80 | s | C-2 C |
| 143.06 | s | C-2 B |
| 143.12 | s | C-6 B |
| 144.42 | s | C-6 C |
| 144.98 | s | C-6 D |
| 149.74 | s | C-8 B |
| 149.79 | s | C-8 C |
| 151.66 | s | C-8 D |
| 171.97 | s | C-7 A |

EXAMPLE 2 OF A DYE COMPOSITION

The direct dye composition below for hair was prepared:

| | |
|---|---|
| Compound of formula (II) 10$^{-3}$ mol | 0.6 g |
| Benzyl alcohol | 14 g |
| Ethanol | 46 g |
| Demineralized water qs | 100 g |

The above composition was applied to locks of natural or permanent-waved grey hair containing 90% white hairs, at a rate of 5 g of composition per gram of hair, and was left to stand on the locks for 30 minutes. After rinsing with running water and drying, the hair was dyed in a deep red shade.

What is claimed is:

1. A compound of formula (I):

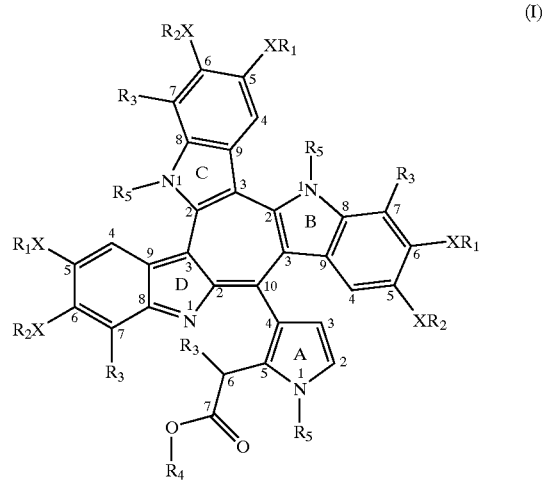

(I)

wherein:

X, which may be identical or different, are each chosen from oxygen atoms and nitrogen atoms;

R$_1$ and R$_2$, which may be identical or different, are each chosen from hydrogen atoms, C$_1$–C$_4$ alkyl groups, C$_1$–C$_4$ monohydroxyalkyl groups, C$_1$–C$_4$ polyhydroxyalkyl groups, acyl(C$_1$–C$_4$ alkyl carbonyl) groups, C$_1$–C$_4$ aminoalkyl groups, C$_1$–C$_4$ polyaminoalkyl groups and C$_1$–C$_4$ aminohydroxyalkyl groups;

R$_3$, R$_4$ and R$_5$, which may be identical or different, are each chosen from hydrogen atoms and linear and branched, saturated and unsaturated C$_1$–C$_4$ hydrocarbons.

2. A compound according to claim 1, wherein said C$_1$–C$_4$ alkyl groups are chosen from methyl groups, ethyl groups, n-propyl groups, isopropyl groups, n-butyl groups, isobutyl groups and tert-butyl groups.

3. A compound according to claim 1, wherein said C$_1$–C$_4$ monohydroxyalkyl groups are —CH$_2$—CH$_2$OH groups.

4. A compound according to claim 1, wherein said C$_1$–C$_4$ polyhydroxyalkyl groups are —CHOH—CH$_2$OH groups.

5. A compound of formula (II):

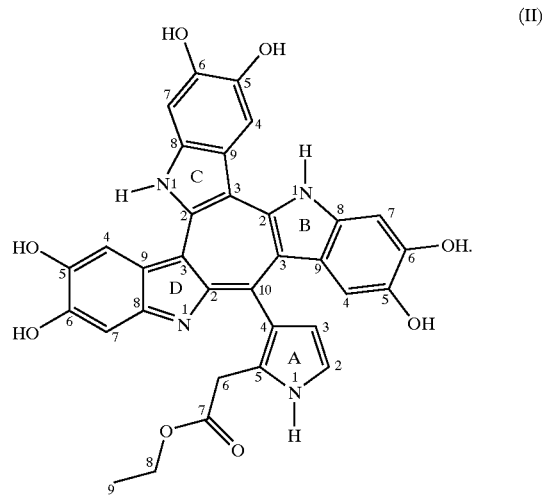

(II)

6. A process of manufacturing a compound of formula (I):

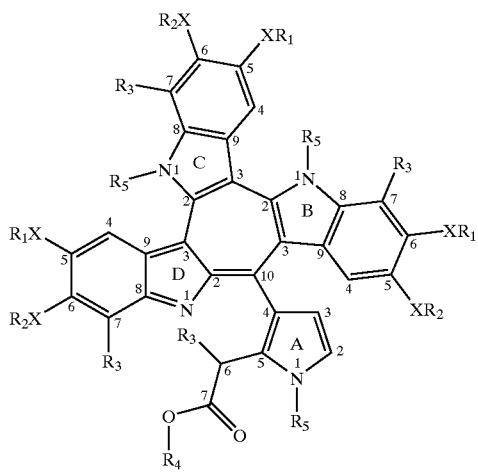

(I)

wherein:

X, which may be identical or different, are each chosen from oxygen atoms and nitrogen atoms;

$R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl($C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;

$R_3$, $R_4$ and $R_5$, which may be identical or different, are each chosen from hydrogen atoms and linear and branched, saturated and unsaturated $C_1$–$C_4$ hydrocarbons; comprising oxidizing a compound of formula (III):

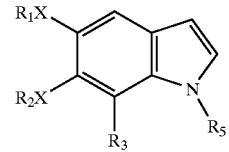

(III)

wherein $R_1$, $R_2$, $R_3$, $R_5$ and X are as defined in said formula (I), under conditions sufficient to obtain said compound of formula (I).

7. A process according to claim 6, wherein said oxidizing occurs in an alcoholic medium.

8. A process according to claim 7, wherein said alcoholic medium is chosen from methanol, ethanol, n-propanol, isopropanol, n-butanol and tert-butanol.

9. A process according to claim 6, wherein said process occurs at room temperature.

10. A process according to claim 6, wherein said oxidizing involves at least one oxidizing agent compound chosen from sodium metaperiodate and sodium metaperiodate substitutes.

11. A process according to claim 10, wherein said sodium metaperiodate substitutes are chosen from molecular oxygen, hydrogen peroxide, potassium permanganate, selenium oxide and peracids.

12. A process according to claim 10, wherein said oxidizing further involves at least one metal catalyst.

13. A process according to claim 12, wherein said at least one metal catalyst is chosen from manganese, iron and chromium.

14. A process according to claim 6, wherein said compound of formula (III) oxidizing occurs in an alcoholic medium, in the presence of sodium metaperiodate, and at room temperature.

* * * * *